United States Patent
Moon et al.

(10) Patent No.: US 7,848,811 B2
(45) Date of Patent: Dec. 7, 2010

(54) POSTURE SENSOR

(75) Inventors: Loell Boyce Moon, Ham Lake, MN (US); David C Johnson, Inver Grove Heights, MN (US); Veerichetty Kadhiresan, Centerville, MN (US); Karen Franke, Tampa, FL (US); Brandi Tait, Harrisburg, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 994 days.

(21) Appl. No.: 11/314,170

(22) Filed: Dec. 21, 2005

(65) Prior Publication Data

US 2007/0142868 A1    Jun. 21, 2007

(51) Int. Cl.
*A61N 1/365* (2006.01)
(52) U.S. Cl. ....................................................... 607/19
(58) Field of Classification Search .............. 607/17–20
See application file for complete search history.

(56) References Cited

U.S. PATENT DOCUMENTS

| 4,428,378 | A | 1/1984 | Anderson et al. |
| 5,472,453 | A | 12/1995 | Alt |
| 5,593,431 | A * | 1/1997 | Sheldon ........................ 607/19 |
| 5,725,562 | A | 3/1998 | Sheldon |
| 5,865,760 | A * | 2/1999 | Lidman et al. .............. 600/509 |
| 6,044,297 | A | 3/2000 | Sheldon et al. |
| 6,351,672 | B1 | 2/2002 | Park et al. |
| 6,408,208 | B1 * | 6/2002 | Sun .............................. 607/17 |
| 6,466,821 | B1 | 10/2002 | Pianca et al. |
| 6,625,493 | B2 | 9/2003 | Kroll et al. |
| 6,658,292 | B2 | 12/2003 | Kroll et al. |
| 2004/0106962 | A1 | 6/2004 | Mai et al. |
| 2004/0111040 | A1 | 6/2004 | Ni et al. |
| 2005/0060001 | A1 | 3/2005 | Singhal et al. |
| 2005/0148897 | A1 | 7/2005 | Cho et al. |

* cited by examiner

*Primary Examiner*—Carl H Layno
*Assistant Examiner*—Joseph Stoklosa
(74) *Attorney, Agent, or Firm*—Schwegman, Lundberg & Woessner, P.A.

(57) ABSTRACT

A system and method determines the posture of a body. The system is first calibrated by attaching it to, or implanted it into, a body, placing the body in particular postures, and generating spectral signatures for each of those postures. Thereafter, the system generates spectral signatures for particular instants in time, correlates these instant signatures with the stored signatures, from which the posture of the body at that instant in time is determined.

28 Claims, 4 Drawing Sheets

POSTURE SENSOR

TECHNICAL FIELD

Various embodiments relate to the field of medical devices, and in particular, but not by way of limitation, to implantable medical devices with diagnostic capabilities.

BACKGROUND

Orthostatic state (i.e. posture) impacts measurement and analysis of physiologic parameters (e.g., heart rate, blood pressure, and trans-thoracic impedance). Consequently, when recording physiologic parameters, attention should be paid to the posture of the patient. For example, when a practitioner takes the blood pressure of a patient in a prone position, the patient should be instructed to not cross his legs since the elevation of one of the legs will affect the blood pressure reading. The monitoring of these physiological parameters is also sometimes important to persons who have an implanted medical device such as a pacemaker. Such medical devices not only can provide pacing and other therapies to a patient, but also can sense physiologic parameters such as the heart rate, and adjust the therapy of the device accordingly. The present inventors have recognized that such therapeutic and diagnostic medical devices should accurately monitor physiologic parameters under various orthostatic conditions.

SUMMARY

In an example, an implantable medical device includes an accelerometer. The device is attached to or implanted into a body, and the body is placed in particular postures. The accelerometer experiences accelerations due to characteristic motions of the body, heart, and lungs in that particular posture. This causes the accelerometer to generate a time domain acceleration signal, which is input into a transform module to produce a frequency domain acceleration spectral signature for that particular posture. This posture spectral signature is stored into a memory circuit associated with the device. The body is then placed in other postures, and spectral signatures are generated and stored for these other postures. After spectral signatures are generated for all postures of interest, if not presently implanted, the device may be implanted into a body.

After the calibration of the device with the posture spectral signatures, the accelerometer experiences accelerations generated by later postures of the body. The time domain signals generated by these accelerations are transformed into frequency domain spectral signatures, and compared to the stored spectral signatures developed during the calibration phase. A later posture of the body may then be determined by correlating the instant spectral signature with the one or more stored spectral signatures.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe similar components throughout the several views. The drawings illustrate generally, by way of example, but not by way of limitation, various examples discussed in the present document.

DETAILED DESCRIPTION

Figure 1:
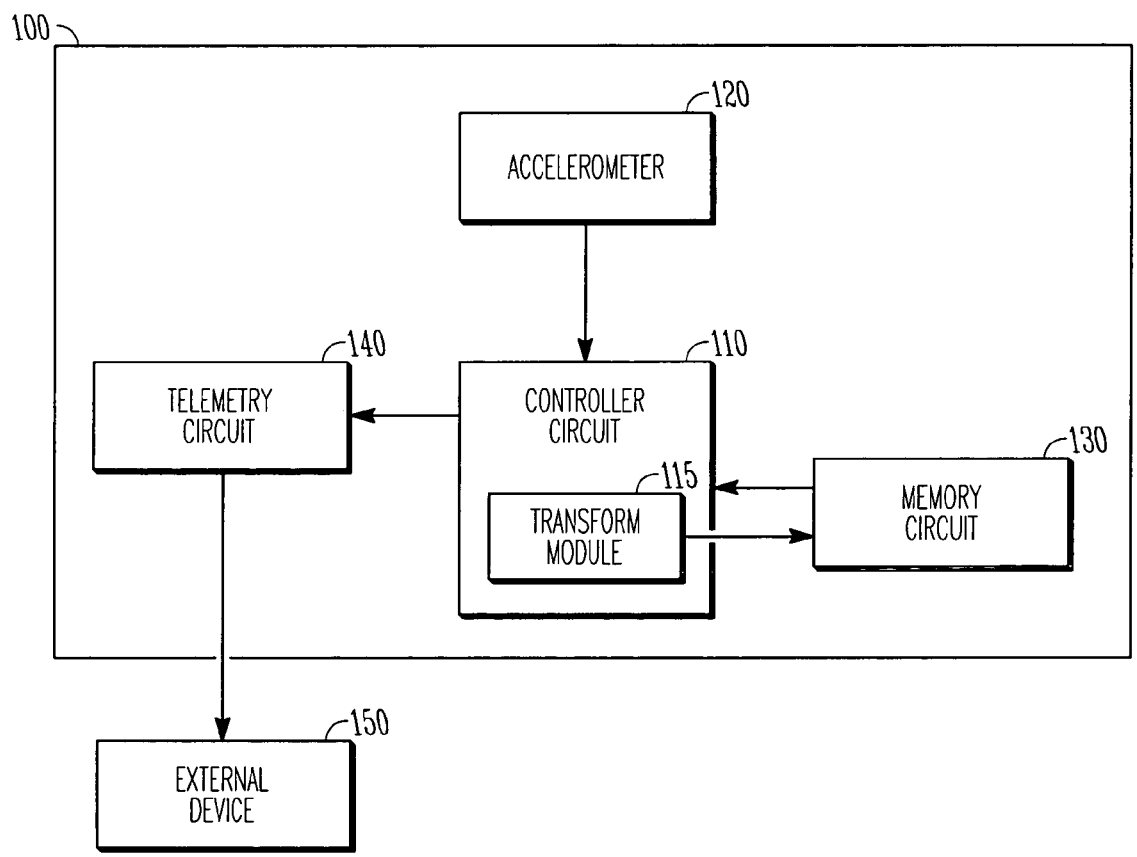
FIG. 1 is a block diagram illustrating an example of a posture discriminator.

In the following detailed description, reference is made to the accompanying drawings which form a part hereof, and in which is shown by way of illustration specific embodiments in which the invention may be practiced. These embodiments are discussed in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document describes a system and method to determine the posture of a body. The ability to determine a posture of a body provides at least two useful applications. First, the amount of time that a particular person spends per day in a standing posture versus a lying posture is an indication of the general overall health status of the individual. Therefore, determining the percentages of time spent in these postures on an ongoing basis would be useful in determining the health status of a person. Second, implanted device-based systems that monitor and/or measure various physiological parameters should be able to identify the posture of the body during which such measurements were taken, since body posture often has a measurable effect on such physiological parameters such as heart rate, blood pressure, and trans-thoracic impedance.

The present inventors have recognized that a body will exhibit a unique motion spectral signature for each different posture position of the body. That is, a motion sensing device signal generated by a particular posture has a recognizable amplitude versus frequency signature due to characteristic motions conducted in the particular posture. In various embodiments, the motion sensing device may be an accelerometer, a mercury switch, or some other motion sensing device. Specifically, the accelerometer senses an acceleration due to body movement, cardiac (heart contraction) movement, and pulmonary (breathing) movement. Each one of these movements differ depending on the posture of a body. In an example, these differences are exploited to determine that posture. For example, except for a soldier standing at attention, a person who is standing is normally not completely still, but rather moves his arms, legs, and body position while he is standing. By comparison, a person who is sitting, whether engaged in conversation, reading, or watching television, does not typically move around as much as a person who is standing. Consequently, the motion spectral signature of a standing posture is discernable from the motion spectral signature of a sitting posture. Similarly, other postures can be discriminated based on their characteristic motion spectral signatures.

In an example, an accelerometer is attached to or implanted into a body. The body is then placed in a particular known posture, and the output from the accelerometer is transformed into a unique spectral signature for that known posture and stored in memory. This is repeated for several distinct known postures, and these spectral signatures for these additional known postures are also stored in memory. This may be referred to as a characterization or acquisition phase. The output of the attached/implanted accelerometer at that later time is then compared to the stored, acquired unique postural spectral signatures, and the later posture can be determined from this comparison. This may be referred to as a matching or correlation phase.

FIG. 1 illustrates an example of a medical device 100. The device 100 includes a controller circuit 110 including a transform module 115. An accelerometer 120 is connected to the controller circuit 110. The transform module 115 transforms an acceleration output signal in the time domain into an output in the frequency domain. The transform module 115 is coupled to a memory circuit 130. The controller circuit 110 is further coupled to a telemetry circuit 140, which in turn is wirelessly coupled to an adjunct device 150 via telemetry. FIG. 1 illustrates one example of a medical device 100. Other examples also exist such as one in which the transform module 115 and memory circuit 130 are physically associated with the adjunct device 150 in lieu of the device 100.

Figure 3:
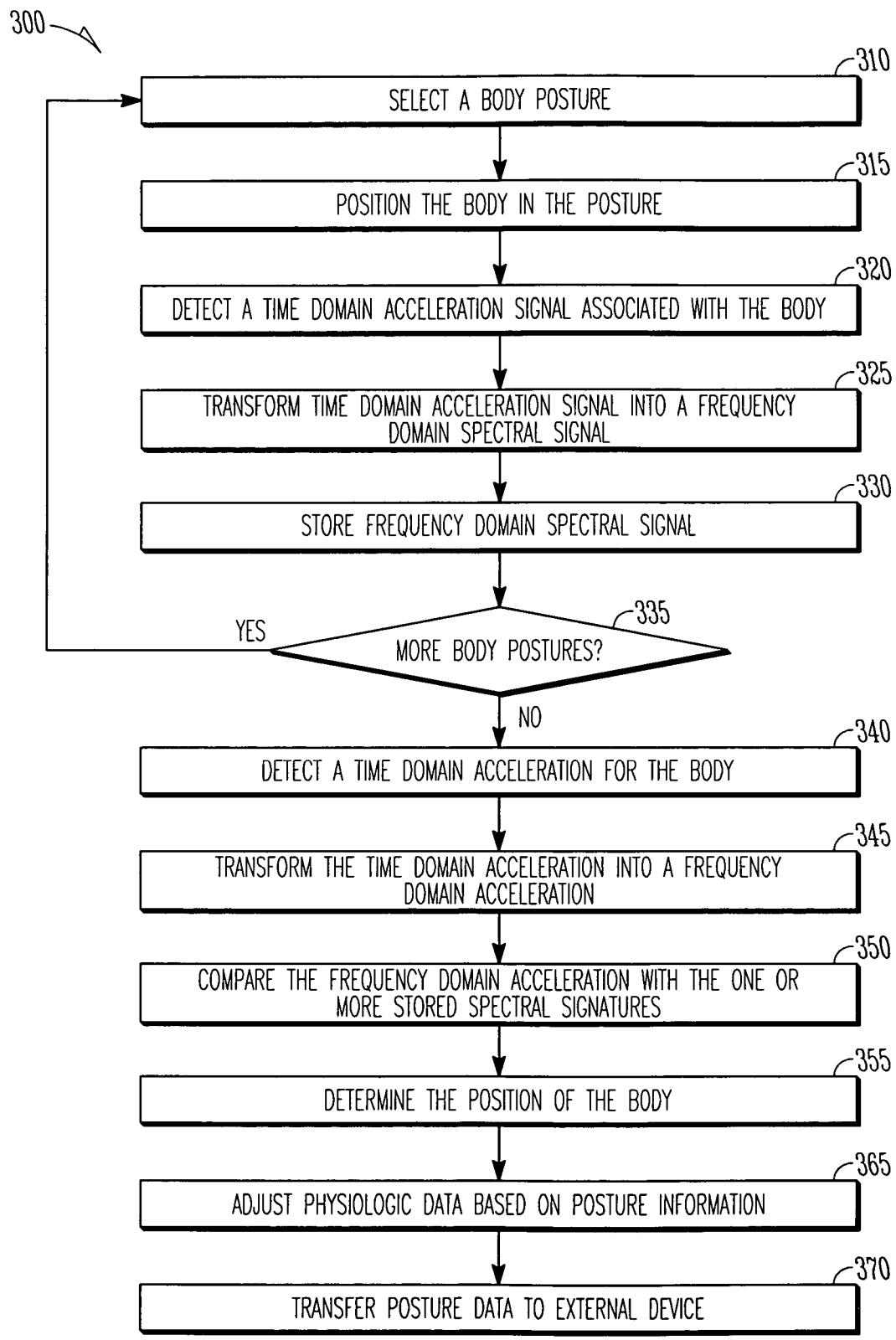
FIG. 3 illustrates an example of a process flow for determining the posture of a body.

FIG. 3 illustrates a flowchart of an example process 300 for calibrating a posture sensing device, and then detecting body postures with the device. In an example, the medical device 100 is associated with a body. This association may be via a temporary external attachment to the body, implantation into the body, or some other technique of attachment to the body. After attachment of the device 100 to the body, a posture is selected at 310 (e.g., a standing posture), and the body is placed in that particular posture position at 315. The accelerometer 120 senses accelerations resulting from the movements associated with the posture of the body at 320, and the accelerometer generates a resulting acceleration signal in the time domain. The controller 110 receives the time domain accelerometer signal, and forwards it onto the transform module 115.

The transform module 115 may be hardware-based, software-based, or a combination of hardware and software. The transform module transforms the time domain acceleration signal into a frequency domain acceleration spectral signature at 325. The frequency domain acceleration spectral signature is stored at 330 in memory 130. The process then determines if there are additional postures to calibrate at 335, and if there are, this process is repeated for other body postures of interest (such as a sitting posture, a lying posture, and an ambulatory posture). In this example, spectral signatures are typically individually developed for each particular patient's body. In an example in which the device 100 is implanted into the body before the characterization phase, the calibration of the device can be accomplished by communicating with the device 100 through the telemetry circuit 140.

Figure 2A:
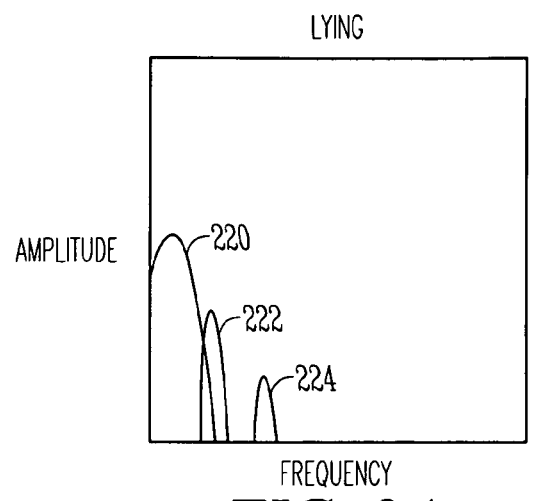
FIGS. 2A, 2B, and 2C illustrate examples of spectral signatures.
Figure 2B:
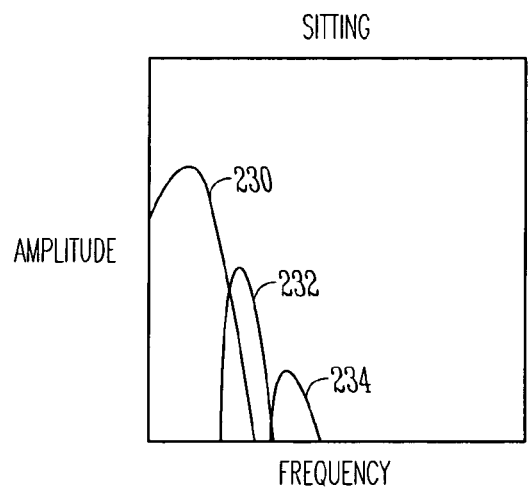
Figure 2C:
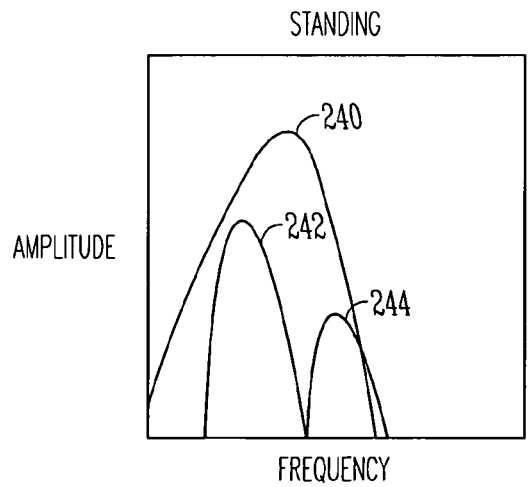

The frequency domain acceleration spectral signal will have components from body movement, cardiac movement, and pulmonary movement. An example of spectral signatures are illustrated in FIGS. 2A, 2B, and 2C. FIG. 2A illustrates an example of the spectral components of a frequency domain spectral signature generated by a body in the lying posture. The horizontal axis represents the frequency range or spectrum, and the vertical axis represents the occurrence of each frequency as represented by an amplitude. FIG. 2A illustrates the body motion component 220, the pulmonary motion component 222, and the cardiac motion component 224. FIG. 2B illustrates an example of a spectral signature for a body in a sitting posture, illustrating a body motion component 230, a pulmonary motion component 232, and a cardiac motion component 234. Similarly, FIG. 2C illustrates an example of a spectral signature for a body in a standing posture, illustrating a body motion component 240, a pulmonary motion component 242, and a cardiac motion component 244.

After calibration of the device 100 for one or more specific postures, the device is ready to correlate these calibrated spectral signatures for these specific postures with later motion signatures sensed by the accelerometer 120 and transformed by the transform module 115. In the correlation phase, the accelerometer outputs a time domain motion signature which is detected at 340 by the controller circuit 110. The transform module 115 of the controller circuit transforms the time domain signal of the accelerometer into a frequency domain acceleration spectral signature at 345. In an example, the conversion of the time domain output into a frequency domain spectral signature is accomplished with a Fast Fourier Transform (FFT) module. This spectral of the body in a particular posture is then correlated at 350 with the spectral signatures that were generated and stored in memory 130 during the characterization phase. By determining which posture stored in memory best correlates with the later spectral signature, a determination can be made at 355 as to whether the later corresponding posture is standing, sitting, lying, ambulatory, or some other posture that was stored in memory during the characterization phase.

In an example, the device 100 operates as part of a cardiac function management device at 365 to properly frame, interpret, and adjust physiological data that is monitored and collected by the cardiac function management device. For example, a cardiac device may monitor and/or record the heart rate or blood pressure of a patient. This data can be used in pacing or other therapies, or simply may be stored for later analysis by the attending physician. However, since the heart rate and other physiological parameters depend in part on the posture of the patient, recording the heart rate without knowing the posture of the patient is of limited value. Therefore, in certain examples, the device 100 can be used to record the posture of a body at the time that the physiologic measure such as heart rate is recorded. This posture information can then be used in the pacing and other therapies associated with the cardiac device. The posture information can also be used to adjust the physiologic data that is otherwise confounded with posture effects. This adjustment can either be done automatically by the device 100, or later by the physician after analyzing the data.

Figure 4:
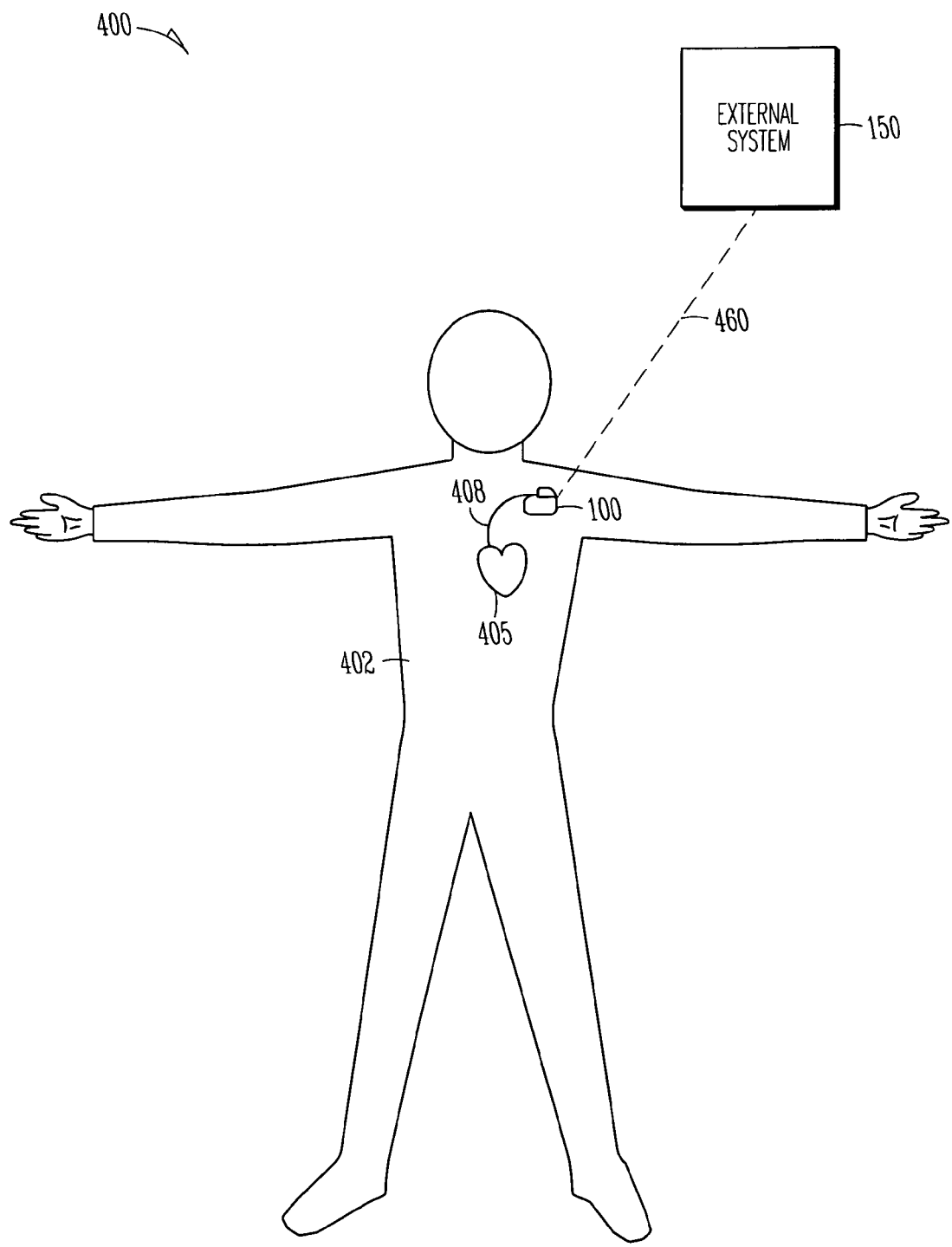
FIG. 4 illustrates an example embodiment of an implanted posture discriminator coupled to an adjunct device.

FIG. 4 is a block diagram illustrating an example of a medical device system 400, and portions of an environment in which it is used. In this environment, the environment includes a body 402 with a heart 405. System 400 includes an implantable medical device 100, a lead system 408, an adjunct device or system 150, and a wireless telemetry link 460. In an example, the posture information is communicated at 370 (FIG. 3) to the adjunct device 150 via telemetry circuit 140. The posture data loaded into the device 150 can then be used for analysis and interpretation either immediately or at a later time.

In the foregoing detailed description of embodiments of the invention, various features are grouped together in one or more embodiments for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the detailed description of embodiments of the invention, with each claim standing on its own as a separate embodiment. It is understood that the above description is intended to be illustrative, and not restrictive. It is intended to cover all alternatives, modifications and equivalents as may be included within the scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

The abstract is provided to comply with 37 C.F.R. 1.72(b) to allow a reader to quickly ascertain the nature and gist of the technical disclosure. The Abstract is submitted with the understanding that it will not be used to interpret or limit the scope or meaning of the claims.

What is claimed is:

1. A system comprising:
   a medical device, the medical device comprising:
   an accelerometer configured to produce a time domain acceleration signal;
   a controller circuit comprising a time-domain-to-frequency-domain transform module coupled to the accelerometer, wherein the transform module is configured to transform the time domain acceleration signal into a frequency domain acceleration spectrum; and
   a memory circuit, coupled to the transform module, the memory comprising first spectral signatures, each first spectral signature representative of a specified posture, wherein each of the first spectral signatures includes frequency domain acceleration information resulting from body motion, cardiac motion, and respiratory motion while the body is in the specified posture, and
   wherein the controller circuit is configured to compare the frequency domain acceleration spectrum with each of the first spectral signatures to determine which stored first spectral signature best correlates with the frequency domain acceleration spectrum to determine a posture of the body.

2. The system of claim 1, wherein the postures comprise a standing posture, a sitting posture, a lying posture and an ambulatory posture.

3. The system of claim 1, wherein the transform module is operable to perform a Fast Fourier Transform to transform a time domain output of the accelerometer into a frequency domain output of the accelerometer.

4. The system of claim 1, wherein the memory comprises at least one second spectral signature including information about a later posture of the body, and wherein the controller is operable to compare the second spectral signature with the first spectral signatures to determine the instant posture of the body.

5. The system of claim 4, wherein the controller is operable to compare the second spectral signature with the first spectral signatures by computing at least one correlation between the second spectral signature and the one or more first spectral signatures.

6. The system of claim 5, wherein the medical device includes an implantable cardiac function management device.

7. The system of claim 6, wherein the accelerometer may also at least partially controls a rate of pacing by the implantable cardiac function management device.

8. The system of claim 4, wherein the memory records physiologic data.

9. The system of claim 8, wherein the controller adjusts the physiologic data using the determined posture of the body.

10. The system of claim 1, wherein the controller circuit is configured to provide an output distinguishing at least one of standing, sitting, and lying from another of standing, sitting, and lying.

11. The system of claim 4, in which the memory records one or more statistics relating to how long the body is in a particular posture over a particular period of time.

12. The system of claim 4, comprising a communication circuit operable to communicate information about the determined posture from an implantable medical device to an adjunct device.

13. The system of claim 4, in which the controller circuit is implantable.

14. A method comprising:
   detecting a time domain acceleration signal representative of physiologic movement of a body;
   transforming the time domain acceleration signal into a frequency domain acceleration spectrum; and
   comparing the frequency domain acceleration spectrum with stored spectral signatures to obtain posture information about the body, each stored spectral signature representative of a specified posture, wherein each of the spectral signatures includes frequency domain acceleration information resulting from body motion, cardiac motion, and respiratory motion while the body is in the specified posture, wherein comparing includes comparing the frequency domain acceleration spectrum with each of the stored spectral signatures to determine which stored spectral signature best correlates with the frequency domain acceleration spectrum to determine a posture of the body.

15. The method of claim 14, wherein comparing the frequency domain acceleration with the stored spectral signatures includes comparing one or more of a standing posture spectral signature, a sitting posture spectral signature, a lying posture spectral signature, and an ambulatory posture spectral signature.

16. The method of claim 14, comprising recording one or more statistics relating to how long the body is in a particular posture over a particular period of time.

17. The method of claim 14, in which the detecting the time domain acceleration comprises using an implantable accelerometer.

18. The method of claim 17, comprising at least partially controlling a rate of pacing using information from the same implantable accelerometer.

19. The method of claim 14, comprising:
   positioning the body in a known particular posture;
   detecting a time domain acceleration associated with the body in the particular posture;
   transforming the time domain acceleration in the particular posture into a frequency domain acceleration in the particular posture to obtain the specified spectral signature corresponding to the particular posture; and
   storing the spectral signature corresponding to the particular posture, wherein the stored spectral signature is available for comparison with a subsequent frequency domain acceleration to obtain posture information about the body when it is undergoing the subsequent frequency domain acceleration.

20. The method of claim 14, wherein the comparing comprises computing a correlation between the frequency domain acceleration spectrum and the stored spectral signatures.

21. The method of claim 14, including providing an indication distinguishing at least one of standing, sitting, and lying from another of standing, sitting, and lying.

22. The method of claim 14, comprising:
recording physiologic data; and
adjusting the physiologic data using the posture information about the body.

23. The method of claim 14, comprising communicating the posture information about the body between an implanted medical device and an adjunct device.

24. An implantable cardiac function management device comprising:
an accelerometer, providing a time domain acceleration signal of a living body;
a controller circuit, coupled to the accelerometer, comprising a time-domain-to-frequency-domain transform module coupled to said accelerometer; and
a memory circuit, coupled to the transform module, the memory comprising:
first spectral signatures each representative of a specified posture, wherein each of the first spectral signatures includes frequency domain acceleration information resulting from body motion, cardiac motion, and respiratory motion while the body is in the specified posture, including at least one of a standing posture, a sitting posture, a lying posture, and an ambulatory posture; and
at least one second spectral signature of physiologic movement including information about an instant posture of the body, and wherein the controller circuit is operable to correlate the second spectral signature with the first spectral signatures to determine which stored first spectral signature best correlates with the second spectral signature to determine the instant posture of the body.

25. The device of claim 24, wherein the accelerometer also at least partially controls a rate of pacing by the implantable cardiac function management device.

26. The device of claim 24, wherein the controller adjusts the physiologic data using the determined posture of the body.

27. A system comprising:
a medical device, the medical device comprising:
a motion sensing device configured to produce a time domain motion signal;
a controller circuit comprising a time-domain-to-frequency-domain transform module coupled to the motion sensing device, wherein the transform module is configured to transform the time domain motion signal into a frequency domain motion spectrum; and
a memory circuit, coupled to the transform module, the memory comprising first spectral signatures, each first spectral signature representative of a specified posture, wherein each of the first spectral signatures includes frequency domain acceleration information resulting from body motion, cardiac motion, and respiratory motion while the body is in the specified posture, and
wherein the controller circuit is configured to compare the frequency domain motion spectrum with each of the first spectral signatures to determine which stored first spectral signature best correlates with the frequency domain acceleration spectrum to determine a posture of the body.

28. The system of claim 27, wherein said motion sensing device comprises an accelerometer.

* * * * *